United States Patent
Polisetti et al.

(10) Patent No.: US 9,162,963 B2
(45) Date of Patent: Oct. 20, 2015

(54) PHENYLGLYOXYLIC ACID DERIVATIVES AND THEIR PREPARATION AND USE

(71) Applicant: TransTech Pharma, LLC, High Point, NC (US)

(72) Inventors: Dharma Rao Polisetti, High Point, NC (US); Kalpathy Santhosh, Jamestown, NC (US); Muralidhar Bondlela, Greensboro, NC (US); Robert Carl Andrews, Jamestown, NC (US); Thomas Scott Yokum, Greensboro, NC (US); Eugene Campian, Jamestown, NC (US); Rajashaker Kache, Cary, NC (US)

(73) Assignee: vTv Therapeutics LLC, High Point, NC (US)

( * ) Notice: Subject to any disclaimer, the term of this patent is extended or adjusted under 35 U.S.C. 154(b) by 0 days.

(21) Appl. No.: 13/934,491

(22) Filed: Jul. 3, 2013

(65) Prior Publication Data

US 2013/0296599 A1    Nov. 7, 2013

Related U.S. Application Data

(63) Continuation of application No. PCT/US2012/020307, filed on Jan. 5, 2012.

(60) Provisional application No. 61/432,057, filed on Jan. 12, 2011, provisional application No. 61/432,941, filed on Jan. 14, 2011, provisional application No. 61/524,010, filed on Aug. 16, 2011.

(51) Int. Cl.
*C07C 69/738* (2006.01)
*C07C 59/68* (2006.01)
*C07C 67/313* (2006.01)
*C07C 67/31* (2006.01)

(52) U.S. Cl.
CPC ............... *C07C 59/68* (2013.01); *C07C 67/31* (2013.01); *C07C 67/313* (2013.01); *C07C 69/738* (2013.01); *C07B 2200/07* (2013.01)

(58) Field of Classification Search
CPC ............................. C07C 69/738; C07C 59/68
USPC ............................................. 560/53; 562/470
See application file for complete search history.

(56) References Cited

U.S. PATENT DOCUMENTS 5,344,843 A * 9/1994 Guthrie et al. ................ 514/473

FOREIGN PATENT DOCUMENTS

| WO | WO 2008/051563 | 5/2008 |
| WO | WO 2009/111700 | 9/2009 |
| WO | WO 2011/156655 | 12/2011 |

OTHER PUBLICATIONS

Freeman, Jennifer L.R. et al., "TTP3859: Identification of a Non-Peptide GLP-1 Receptor Agonist That Enhances Glycemic Control in vivo," 4th G Protein-Coupled Receptors: An ASPET Colloquium, Apr. 24-25, 2013, abstract. p. 51 (2013).
Freeman, Jennifer L.R. et al., "TTP3859: Identification of a Non-Peptide GLP-1 Receptor Agonist That Enhances Glycemic Control in vivo," 4th G Protein-Coupled Receptors: An ASPET Colloquium, Apr. 24-25, 2013, poster 61 (2013).
International Search Report for related International Application No. PCT/US2012/020307 mailed May 29, 2012.
Wootten, Denise et al., "Differential Activation and Modulation of the Glucagon-Like Peptide-1 Receptor by Small Molecule Ligands" Molecular Pharmacology, vol. 83, pp. 822-834 (2013).
Written Opinion for related International Application No. PCT/US2012/020307 mailed May 29, 2012.

* cited by examiner

*Primary Examiner* — Yong Chu
(74) *Attorney, Agent, or Firm* — Samuel B. Rollins

(57) ABSTRACT

The invention provides novel phenylglyoxylic acid derivatives, which may be useful as intermediates for preparing stereoisomerically enriched drug compounds. The invention also provides methods of making phenylglyoxylic acid derivatives, and uses of phenylglyoxylic acid derivatives.

6 Claims, No Drawings

PHENYLGLYOXYLIC ACID DERIVATIVES AND THEIR PREPARATION AND USE

FIELD OF THE INVENTION

The invention relates to novel phenylglyoxylic acid derivatives, and methods of making and using such compounds.

BACKGROUND OF THE INVENTION

Optically active compounds are useful as starting materials or as intermediates for making drug compounds, pesticides, herbicides, and the like. For example, optically active phenylalanine may be used to make 2-amino-4-phenylbutanoate derivatives, such as enalapril. See H. Urbach & R. Henning, *Tetrahedron Letters*, Vol. 25, p. 1143 (1984).

WO 2009/111700 describes various oxadiazoanthracene derivatives which are active as modulators of the human GLP-1 receptor. When such compounds are substituted at the 3-position of the oxadiazoanthracene ring system, a stereocenter results. In many instances, the substituent at the 3-position is a substituted benzyloxyphenyl moiety. In synthesizing these molecules, it is desirable to employ intermediates that are stereoisomerically enriched in the desired epimer. Thereby one may improve the yield of the resulting stereoisomer, which reduces material use and waste.

WO 2008/051563 discloses optically active mandelic acid derivatives and methods of making such compounds. Such compounds (or derivatives thereof) may be used to synthesize stereoisomerically enriched (or even stereoisomerically pure) mandelic acid derivatives that may be used to synthesize many of the oxadiazoanthracene derivatives described in the above publication. WO 2008/051563 describes a synthetic method that employs an enzyme, particularly a lipase. While such enzyme-mediated syntheses may be useful in many contexts, it may also be useful to employ other means to make stereoisomerically enriched optically active mandelic acid derivatives. For example, in larger-scale syntheses, it may be useful to make stereoisomerically enriched optically active mandelic acid derivatives without having to employ an enzyme.

Therefore, there is a continuing need for new chemical intermediates and synthetic methods employing such intermediates, where such compounds and methods may be useful for making stereoisomerically enriched optically active mandelic acid derivatives.

SUMMARY OF THE INVENTION

In one aspect, the invention provides novel phenylglyoxylic acid derivatives that may be useful as intermediates for making stereoisomerically enriched drug compounds. These phenylglyoxylic acid derivatives have a structure that corresponds to Formula (I), where the various substituents are defined in detail below.

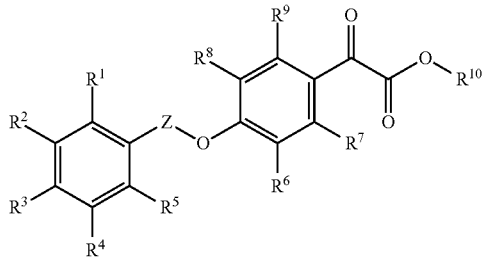

(I)

In another aspect, the invention provides methods of making compounds of Formula (I) from a corresponding mandelic acid derivative. In some embodiments, compounds of Formula (I) are made using activated manganese (IV) oxide. In some other embodiments, compounds of Formula (I) are made using 2,2,6,6-tetramethylpiperidine-1-oxyl (TEMPO) in combination with an oxidizing solution (e.g., a bleach solution).

In another aspect, the invention provides methods of using compounds of Formula (I) to make a stereoisomerically enriched mandelic acid derivative. In some embodiments, stereoisomerically enriched mandelic acid derivatives are made from compounds of Formula (I) by employing a chiral reduction.

Additional features and/or aspects of the invention are described below.

DETAILED DESCRIPTION

The following definitions are meant to clarify the terms defined. If a particular term used herein is not specifically defined, the term should not be considered to be indefinite. Rather, such undefined terms are to be construed in accordance with their plain and ordinary meaning that such terms would have to persons of ordinary skill in the art to which the inventions are directed.

As used herein the term "alkyl" refers to a fully saturated straight or branched chain hydrocarbon having one to ten carbon atoms, which may be optionally substituted, as herein further described, with multiple degrees of substitution being allowed. If no substitutions are described, then the alkyl group is unsubstituted. Examples of "alkyl" as used herein include, but are not limited to, methyl, ethyl, n-propyl, iso-propyl, isobutyl, n-butyl, sec-butyl, tert-butyl, isopentyl, n-pentyl, neopentyl, n-hexyl, and 2-ethylhexyl.

The number of carbon atoms in an alkyl group will be represented by the phrase "$C_{x-y}$ alkyl," which refers to an alkyl group, as herein defined, containing from x to y, inclusive, carbon atoms. Thus, $C_{1-6}$ alkyl represents an alkyl chain having from 1 to 6 carbons as described above, and for example, includes, but is not limited to, methyl, ethyl, n-propyl, iso-propyl, isobutyl, n-butyl, sec-butyl, tert-butyl, isopentyl, n-pentyl, neopentyl, and n-hexyl.

As used herein, the term "alkylene" refers to a fully saturated straight or branched chain divalent hydrocarbon radical having from one to ten carbon atoms, which may be optionally substituted as herein further described, with multiple degrees of substitution being allowed. If no substitutions are described, then the alkylene group is unsubstituted. Examples of "alkylene" as used herein include, but are not limited to, methylene, ethylene, n-propylene, 1-methylethylene, 2-methylethylene, dimethylmethylene, n-butylene, 1-methyl-n-propylene, and 2-methyl-n-propylene.

The number of carbon atoms in an alkylene group will be represented by the phrase "$C_{x-y}$ alkylene," which refers to an alkylene group, as herein defined, containing from x to y, inclusive, carbon atoms. Thus, $C_{1-4}$ alkylene represents an alkylene chain having from 1 to 4 carbons as described above, and for example, includes, but is not limited to, methylene, ethylene, n-propylene, 1-methylethylene, 2-methylethylene, dimethylmethylene, n-butylene, 1-methyl-n-propylene, and 2-methyl-n-propylene.

As used herein the term "halogen" refers to fluorine, chlorine, bromine, or iodine.

As used herein the term "haloalkyl" refers to an alkyl group, as defined herein, that is substituted one or more times with halogen. Examples of branched or straight chained "haloalkyl" groups as used herein include, but are not limited to, methyl, ethyl, propyl, isopropyl, n-butyl, and t-butyl substituted independently with one or more halogens, for example, fluoro, chloro, bromo, and iodo. The term "haloalkyl" should be interpreted to include groups such as —CF$_3$, —CH$_2$CF$_3$, and —CF$_2$Cl.

The number of carbon atoms in a haloalkyl group will be represented by the phrase "C$_{x-y}$ haloalkyl," which refers to a haloalkyl group, as herein defined, containing from x to y, inclusive, carbon atoms. Thus, C$_{1-4}$ haloalkyl represents an alkyl chain having from 1 to 4 carbons as described above, and for example, includes, but is not limited to, methyl, ethyl, propyl, isopropyl, n-butyl, and t-butyl substituted independently with one or more halogens, for example, fluoro, chloro, bromo, and iodo.

As used herein, the term "alkoxy" refers to an —O-alkyl substituent, where "alkyl" is defined above. In same manner, the term "C$_{x-y}$ alkoxy" refers to an —O—C$_{x-y}$ alkyl group, where a "C$_{x-y}$ alkyl" group is defined above.

As used herein, the term "haloalkoxy" refers to an —O-haloalkyl substituent, where "haloalkyl" is defined above. In same manner, the term "C$_{x-y}$ haloalkoxy" refers to an —O—C$_{x-y}$ haloalkyl group, where a "C$_{x-y}$ haloalkyl" group is defined above.

As used herein, the term "oxo" refers to a =O substituent.

As used herein, the term "substituted" refers to substitution of one or more hydrogens of the designated moiety with the named substituent or substituents, multiple degrees of substitution being allowed unless otherwise stated, provided that the substitution results in a stable or chemically feasible compound. A stable compound or chemically feasible compound is one in which the chemical structure is not substantially altered when kept at a temperature from about −80° C. to about +40° C., in the absence of moisture or other chemically reactive conditions, for at least a week, or a compound which maintains its integrity long enough to be useful for therapeutic or prophylactic administration to a patient. As used herein, the phrases "substituted with one or more . . . " or "substituted one or more times . . . " refer to a number of substituents that equals from one to the maximum number of substituents possible based on the number of available bonding sites, provided that the above conditions of stability and chemical feasibility are met.

As used herein, the various functional groups represented will be understood to have a point of attachment at the functional group having the hyphen or dash (—) or an asterisk (*). In other words, in the case of —CH$_2$CH$_2$CH$_3$, it will be understood that the point of attachment is the CH$_2$ group at the far left. If a substituent group is recited without an asterisk or a dash, then its attachment point is the attachment point that skilled artisans would generally associate with that group. For example, "methyl" is —CH$_3$, as that conforms to the generally understood meaning of what a methyl group is.

When any variable occurs more than one time in any one constituent (e.g., R$^a$), or multiple constituents, its definition on each occurrence is independent of its definition on every other occurrence.

As used herein, multi-atom bivalent species are to be read from left to right. For example, if the specification or claims recite A-D-E and D is defined as —OC(O)—, the resulting group with D replaced is: A—OC(O)—E and not A—C(O)O—E.

As used herein, the term "optionally" means that the subsequently described event(s) may or may not occur.

As used herein, the term "compound" includes free acids, free bases, and salts thereof. Thus, phrases such as "the compound of embodiment 1" or "the compound of claim 1" are intended to refer to any free acids, free bases, and salts thereof that are encompassed by embodiment 1 or claim 1.

As used herein, the term "phenylglyoxylic acid derivatives" refers to derivatives of phenylglyoxylic acid represented by Formula (I), as described in detail below.

Also included within the scope of the invention are the individual enantiomers of the compounds represented by Formula (I), pharmaceutically acceptable salts thereof, or tautomers of said compounds or salts, as well as any wholly or partially racemic mixtures thereof. The invention also covers the individual enantiomers of the compounds represented by Formula (I), pharmaceutically acceptable salts thereof, or tautomers of said compounds or salts, as well as mixtures with diastereoisomers thereof in which one or more stereocenters are inverted. Unless otherwise stated, structures depicted herein are also meant to include compounds which differ only in the presence of one or more isotopically enriched atoms. For example, compounds having the present structure except for the replacement of a hydrogen atom by a deuterium or tritium, or the replacement of a carbon atom by a $^{13}$C- or $^{14}$C-enriched carbon are within the scope of the invention.

In several aspects, the invention provides phenylglyoxylic acid derivatives, methods of making phenylglyoxylic acid derivatives, and methods of using phenylglyoxylic acid derivatives, particularly for the synthesis of stereoisomerically enriched mandelic acid derivatives.

In a first aspect, the invention provides phenylglyoxylic acid derivatives. Such compounds are useful as intermediates for making stereoisomerically enriched drug compounds.

In a first embodiment (i.e., embodiment 1), the invention provides a compound of Formula (I)

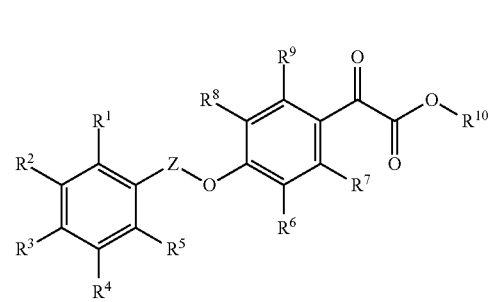

(I)

wherein:
R$^1$ and R$^5$ are hydrogen, halogen, C$_{1-4}$ alkyl, C$_{1-4}$ alkoxy, C$_{1-4}$ haloalkyl, or C$_{1-4}$ haloalkoxy;
R$^3$ is halogen, hydroxyl, cyano, C$_{1-4}$ alkyl, C$_{1-4}$ alkoxy, C$_{1-4}$ haloalkyl, or C$_{1-4}$ haloalkoxy;
one of R$^2$ and R$^4$ is halogen, hydroxyl, cyano, C$_{1-4}$ alkyl, C$_{1-4}$ alkoxy, C$_{1-4}$ haloalkyl, or C$_{1-4}$ haloalkoxy, while the other is hydrogen, halogen, C$_{1-4}$ alkyl, C$_{1-4}$ alkoxy, C$_{1-4}$ haloalkyl, or C$_{1-4}$ haloalkoxy;
R$^6$, R$^7$, R$^8$, R$^9$ are hydrogen, halogen, C$_{1-4}$ alkyl, C$_{1-4}$ alkoxy, C$_{1-4}$ haloalkyl, or C$_{1-4}$ haloalkoxy;
R$^{10}$ is hydrogen, C$_{1-6}$ alkyl, or an alkali metal cation; and
Z is C$_{1-6}$ alkylene, which is optionally substituted one or more times by substituents selected independently from the group consisting of halo, cyano, C$_{1-4}$ haloalkyl, C$_{1-4}$ haloalkoxy, phenyl, and oxo.

Embodiment 2: A compound of embodiment 1, where at least one of R$^2$, R$^3$, or R$^4$ is halogen.

Embodiment 3: A compound of embodiment 2, where at least one of R$^2$, R$^3$, or R$^4$ is chloro.

Embodiment 4: A compound of any one of embodiments 1 to 3, where $R^1$ is hydrogen, fluoro, chloro, methyl, ethyl, isopropyl, methoxy, ethoxy, isopropoxy, trifluoromethyl, or trifluoromethoxy.

Embodiment 5: A compound of embodiment 4, where $R^1$ is hydrogen, fluoro, chloro, methyl, methoxy, trifluoromethyl, or trifluoromethoxy.

Embodiment 6: A compound of embodiment 5, where $R^1$ is hydrogen or chloro.

Embodiment 7: A compound of embodiment 6, where $R^1$ is hydrogen.

Embodiment 8: A compound of any one of embodiments 1 to 7, where $R^5$ is hydrogen, fluoro, chloro, methyl, ethyl, isopropyl, methoxy, ethoxy, isopropoxy, trifluoromethyl, or trifluoromethoxy.

Embodiment 9: A compound of embodiment 8, where $R^5$ is hydrogen, fluoro, chloro, methyl, methoxy, trifluoromethyl, or trifluoromethoxy.

Embodiment 10: A compound of embodiment 9, where $R^5$ is hydrogen or chloro.

Embodiment 11: A compound of embodiment 10, where $R^5$ is hydrogen.

Embodiment 12: A compound of any one of embodiments 1 to 11, where $R^2$ is hydrogen, hydroxyl, cyano, fluoro, chloro, methyl, ethyl, isopropyl, methoxy, ethoxy, isopropoxy, trifluoromethyl, or trifluoromethoxy.

Embodiment 13: A compound of embodiment 12, where $R^2$ is hydrogen, hydroxyl, cyano, fluoro, chloro, methyl, methoxy, trifluoromethyl, or trifluoromethoxy.

Embodiment 14: A compound of embodiment 13, where $R^2$ is hydrogen or chloro.

Embodiment 15: A compound of embodiment 14, where $R^2$ is hydrogen.

Embodiment 16: A compound of any one of embodiments 1 to 15, where $R^4$ is hydrogen, hydroxyl, cyano, fluoro, chloro, methyl, ethyl, isopropyl, methoxy, ethoxy, isopropoxy, trifluoromethyl, or trifluoromethoxy.

Embodiment 17: A compound of embodiment 16, where $R^4$ is hydrogen, hydroxyl, cyano, fluoro, chloro, methyl, methoxy, trifluoromethyl, or trifluoromethoxy.

Embodiment 18: A compound of embodiment 17, where $R^4$ is hydrogen or chloro.

Embodiment 19: A compound of embodiment 18, where $R^4$ is hydrogen.

Embodiment 20: A compound of any one of embodiments 1 to 19, where at least one of $R^2$ or $R^4$ is not hydrogen.

Embodiment 21: A compound of embodiment 20, where $R^2$ is halogen and $R^4$ is hydrogen.

Embodiment 22: A compound of embodiment 20, where $R^2$ is hydrogen and $R^4$ is halogen.

Embodiment 23: A compound of embodiment 21, where $R^2$ is chloro.

Embodiment 24: A compound of embodiment 22, where $R^4$ is chloro.

Embodiment 25: A compound of any one of embodiments 1 to 24, where $R^3$ is hydroxyl, cyano, fluoro, chloro, methyl, ethyl, isopropyl, methoxy, ethoxy, isopropoxy, trifluoromethyl, or trifluoromethoxy.

Embodiment 26: A compound of embodiment 25, where $R^3$ is hydroxyl, cyano, fluoro, chloro, methyl, methoxy, trifluoromethyl, or trifluoromethoxy.

Embodiment 27: A compound of embodiment 26, where $R^3$ is chloro.

Embodiment 28: A compound of any one of embodiments 1 to 24 where $R^3$ is halogen.

Embodiment 29: A compound of any one of embodiments 1 to 28, where $R^6$ is hydrogen, fluoro, chloro, methyl, ethyl, isopropyl, methoxy, ethoxy, isopropoxy, trifluoromethyl, or trifluoromethoxy.

Embodiment 30: A compound of embodiment 29, where $R^6$ is hydrogen, fluoro, chloro, methyl, methoxy, trifluoromethyl, or trifluoromethoxy.

Embodiment 31: A compound of embodiment 30, where $R^6$ is hydrogen, methyl, methoxy, trifluoromethyl, or trifluoromethoxy.

Embodiment 32: A compound of embodiment 30, where $R^6$ is hydrogen, chloro, or fluoro.

Embodiment 33: A compound of embodiment 30, where $R^6$ is hydrogen.

Embodiment 34: A compound of any one of embodiments 1 to 33, where $R^7$ is hydrogen, fluoro, chloro, methyl, ethyl, isopropyl, methoxy, ethoxy, isopropoxy, trifluoromethyl, or trifluoromethoxy.

Embodiment 35: A compound of embodiment 34, where $R^7$ is hydrogen, fluoro, chloro, methyl, methoxy, trifluoromethyl, or trifluoromethoxy.

Embodiment 36: A compound of embodiment 35, where $R^7$ is hydrogen, methyl, methoxy, trifluoromethyl, or trifluoromethoxy.

Embodiment 37: A compound of embodiment 35, where $R^7$ is hydrogen, chloro, or fluoro.

Embodiment 38: A compound of embodiment 35, where $R^7$ is hydrogen.

Embodiment 39: A compound of any one of embodiments 1 to 38, where $R^8$ is hydrogen, fluoro, chloro, methyl, ethyl, isopropyl, methoxy, ethoxy, isopropoxy, trifluoromethyl, or trifluoromethoxy.

Embodiment 40: A compound of embodiment 39, where $R^8$ is hydrogen, fluoro, chloro, methyl, methoxy, trifluoromethyl, or trifluoromethoxy.

Embodiment 41: A compound of embodiment 40, where $R^8$ is hydrogen, methyl, methoxy, trifluoromethyl, or trifluoromethoxy.

Embodiment 42: A compound of embodiment 40, where $R^8$ is hydrogen, chloro, or fluoro.

Embodiment 43: A compound of embodiment 40, where $R^8$ is hydrogen.

Embodiment 44: A compound of any one of embodiments 1 to 43, where $R^9$ is hydrogen, fluoro, chloro, methyl, ethyl, isopropyl, methoxy, ethoxy, isopropoxy, trifluoromethyl, or trifluoromethoxy.

Embodiment 45: A compound of embodiment 44, where $R^9$ is hydrogen, fluoro, chloro, methyl, methoxy, trifluoromethyl, or trifluoromethoxy.

Embodiment 46: A compound of embodiment 45, where $R^9$ is hydrogen, methyl, methoxy, trifluoromethyl, or trifluoromethoxy.

Embodiment 47: A compound of embodiment 45, where $R^9$ is hydrogen, chloro, or fluoro.

Embodiment 48: A compound of embodiment 45, where $R^9$ is hydrogen.

Embodiment 49: A compound of any one of embodiments 1 to 48, where $R^{10}$ is hydrogen.

Embodiment 50: A compound of any one of embodiments 1 to 48, where $R^{10}$ is methyl or ethyl.

Embodiment 51: A compound of embodiment 50, where $R^{10}$ is methyl.

Embodiment 52: A compound of any one of embodiments 1 to 48, where $R^{10}$ is a sodium cation or a potassium cation.

Embodiment 53: A compound of embodiment 52, where $R^{10}$ is a sodium cation.

Embodiment 54: A compound of any one of embodiments 1 to 53, where Z is methylene, 1,2-ethylene, 1,1-ethylene, 1,3-propylene, 1,2-propylene, 1,1-propylene, or 2,2-propylene, where each is optionally substituted one or more times by substituents selected independently from the group consisting of fluoro, chloro, cyano, trifluoromethyl, trifluoromethoxy, phenyl, and oxo.

Embodiment 55: A compound of embodiment 54, where Z is methylene, 1,2-ethylene, or 1,1-ethylene, where each is optionally substituted one or more times by substituents selected independently from the group consisting of fluoro, chloro, trifluoromethyl, trifluoromethoxy, and phenyl.

Embodiment 56: A compound of embodiment 55, where Z is methylene or 1,2-ethylene, where each is optionally substituted one or more times by substituents selected independently from the group consisting of fluoro, chloro, trifluoromethyl, trifluoromethoxy, and phenyl.

Embodiment 57: A compound of embodiment 56, where Z is unsubstituted methylene or unsubstituted 1,2-ethylene.

Embodiment 58: A compound of embodiment 57, where Z is unsubstituted methylene.

The invention includes compounds of embodiments 1 to 58 in any physical forms, for example, as a solid, a liquid, or a gas. In some embodiments, a compound of any one of embodiments 1 to 58 may be dissolved in a solvent. For example, a compound of any one of embodiments 1 to 58 may be at least partly dissolved in a solvent (e.g., ethyl acetate) to improve its solubility or rate of dissolution in another solvent (e.g., diisopropyl ether) used in performing a reaction.

In a second aspect, the invention provides methods of making a compound of any one of embodiments 1 to 58. In some embodiments, a compound of any one of embodiments 1 to 58 is made by oxidizing a corresponding mandelic acid derivative. The invention is not limited to any particular means of performing the oxidation. Suitable oxidation techniques are well known in the art. In some embodiments, the oxidation is carried out in the presence of a metal oxide catalyst. In some such embodiments, the metal oxide catalyst is a transition metal oxide. For example, the metal oxide catalyst can be manganese (IV) oxide. In some embodiments, the oxidation is carried out in the presence of an organic oxidation catalyst. In some such embodiments, the organic oxidation catalyst is a compound having a nitroxyl radical. For example, the organic oxidation catalyst can be 2,2,6,6-tetramethylpiperidinyloxy (TEMPO) or a derivative thereof, such as 4-hydroxy-TEMPO, 4-acetamido-TEMPO, 4-methylsulfonyloxy-TEMPO, 4-(2-bromoacetamido)-TEMPO, 4-(2-iodoacetamido)-TEMPO, 4-amino-TEMPO, 4-carboxy-TEMPO, 4-cyano-TEMPO, 4-benzoyloxy-TEMPO, 4-isothiocyanato-TEMPO, 4-maleimido-TEMPO, 4-methoxy-TEMPO, 4-oxo-TEMPO, 4-phosphonoxy-TEMPO, 4-methacrylate-TEMPO, and the like. In some embodiments where the oxidation is carried out in the presence of an organic oxidation catalyst (according to any of the above embodiments), an inorganic oxidizing agent may also be present. In such embodiments, the inorganic oxidizing agent may be one or more of sodium hypochlorite, hydrogen peroxide, or a peroxide-releasing agent, such as sodium perborate, sodium percarbonate, sodium persulfate, tetrasodium pyrophosphate, urea peroxide, and the like. For example, the inorganic oxidizing agent can be sodium hypochlorite, e.g., as found in commercially available bleach solutions (e.g., 1-10 wt %, or 2-8 wt %, or 3-6 wt %). In other examples, the inorganic oxidizing agent can be hydrogen peroxide, e.g., as a commercially available hydrogen peroxide solutions (e.g., 1-10 wt %, or 2-8 wt %, or 3-6 wt %). In other examples, the inorganic oxidizing agent can be a peroxide-releasing agent, e.g., dissolved in water in a concentration so as to yield a peroxide ion concentration comparable to a 1-10 wt %, or a 2-8 wt %, or a 3-6 wt % solution of hydrogen peroxide.

In a third aspect, the invention provides methods of using a compound of any one of embodiments 1 to 58 to make a stereoisomerically enriched mandelic acid derivative. The invention is not limited to any particular means of performing this chiral or non-racemic reduction. Suitable chiral or non-racemic reduction techniques are well known in the art. In some embodiments, the reduction is carried out in the presence of a stoichiometric reducing agent. Common stoichiometric reducing agents include, but are not limited to, lithium aluminum hydride, sodium borohydride, alkoxy borohydrides, alkoxy aluminum hydrides, and boranes. In some further embodiments, the reduction is carried out in the presence of a chiral or non-racemic catalyst and a suitable reducing agent. For example, the reduction may be carried out in the presence of a catalytic amount of oxazaborolidine in conjunction with borane or catecholborane. As another example, the reduction may be carried out in the presence of a catalytic amount of a transition-metal compound and a reducing agent (e.g., hydrogen gas, formic acid, isopropanol, and other such reducing agents known in the art). Ohkuma and co-workers describe a typical such reduction in the literature, which is incorporated herein by reference. *J. Am. Chem. Soc.*, Vol. 117 at 2675 (1995). Their non-racemic reduction employs $RuCl_2[(S)-BINAP]$ as well as isopropanol, hydrogen gas, potassium hydroxide, and trans-(Ph)$(NH_2)HC$—$CH(Ph)(NH_2)$. As another example, one may employ dichloro(p-cymene)ruthenium(II) dimer and N-((1R, 2R)-2-amino-1,2-diphenylethyl)-2,4,6-triisopropylbenzenesulfonamide. Compounds of the opposite chirality may be prepared by employing chiral catalysts of the opposite chirality. Other such catalysts have been developed in recent years and are well known to skilled artisans as being suitable for chiral or non-racemic reductions of ketones. In other examples, the reduction can be carried out in the presence of a micro-organism, such as baker's yeast.

The chiral or non-racemic reduction need not yield an enantiomerically pure product, although the product may be enantiomerically enriched in one epimer with respect to another. In some embodiments, the reduction will yield a mandelic acid derivative where the ratio of the two epimers is between 3:2 and 1000:1, or between 3:1 and 500:1, or between 5:1 and 500:1, or between 6:1 and 500:1, or between 7:1 and 500:1, or between 9:1 and 500:1, or between 12:1 and 500:1, or between 19:1 and 500:1, or between 33:1 and 500:1, or between 49:1 and 500:1.

EXAMPLES

The following examples are intended to provide further understanding of the embodiments of the invention. They are not intended to limit the scope of the invention in any way, and should not be interpreted as doing so. Although the examples show syntheses carried out using specific compounds, it should be understood that these syntheses can be generalized, so as to permit the skilled artisan to make and use any of the compounds of the invention.

Example 1

Synthesis of
[4-(3,4-Dichlorobenzyloxy)phenyl]-oxo-acetic acid methyl ester

[4-(3,4-Dichlorobenzyloxy)phenyl]-hydroxy-acetic acid methyl ester (85.25 g) was dissolved in dry dichloromethane (500 mL). To the resulting solution, activated manganese (IV) oxide (<5 μm, 175 g) was added. The mixture was stirred vigorously for about 12 hours (until TLC showed no presence of unreacted starting material). The reaction mixture (slurry) was diluted with dichloromethane (500 mL) and was passed through a pad of celite. The filtrate was concentrated to yield the title compound. Proton NMR (400 MHz, CDCl$_3$) was recorded. The following chemical shifts (in ppm) were recorded relative to TMS reference of 0.0 ppm, and include the following: 3.97 (s, 3H); 5.11 (s, 2H); 7.03 (m, 2H); 7.26 (m, 1H); 7.47 (d, 1H); 7.54 (d, 1H); 8.02 (m, 2H).

Example 2

Synthesis of
[4-(3,4-Dichlorobenzyloxy)phenyl]-oxo-acetic acid methyl ester

To [4-(3,4-dichlorobenzyloxy)phenyl]-hydroxy-acetic acid methyl ester (750 g) in ethyl acetate (10 L) was added 2,2,6,6-tetramethylpiperidinyloxy (TEMPO) (10.15 g), KBr (26.25 g), and solid NaHCO$_3$ (185.25 g) in a 22-liter round-bottom flask fitted with an overhead stirrer, thermocouple, and a dropping funnel. The reaction mixture was cooled to 0-5° C. using water/ice. To the cooled reaction mixture, bleach (3375 mL, CLOROX) was added dropwise at such a rate so as to maintain the internal temperature at 0-5° C. After addition of the bleach, the reaction mixture was allowed to reach room temperature and was stirred for 2 hours. LC-MS analysis showed that little of the starting material remained at this point. The reaction mixture was diluted with ethyl acetate (12 L) and the layers were separated. The aqueous layer was washed with ethyl acetate (4 L), and the two volumes of ethyl acetate were combined. The combined ethyl acetate layers were washed with water (10 L) and brine (10 L), dried over anhydrous sodium sulfate, concentrated, and filtered. The resulting solid was washed with hexanes (5 L) and dried at 40° C. under vacuum for 4 hours to yield the title compound.

Example 3

Reduction of
[4-(3,4-Dichlorobenzyloxy)phenyl]-oxo-acetic acid methyl ester

A. Synthesis of N-((1R,2R)-2-amino-1,2-diphenyl-ethyl)-2,4,6-triisopropyl-benzene-sulfonamide.

(1R,2R)-1,2-Diphenyl-ethane-1,2-diamine (1.0 g) was dissolved in dichloromethane (20 mL), and then triethylamine (0.66 mL) added and the mixture was cooled to 5° C. (internal). 2,4,6-Triisopropyl-benzenesulfonyl chloride (1.21 g) was dissolved in dichloromethane (10 mL) and then added to the diamine mixture over 30 minutes, while maintaining the temperature between 7-10 ° C. The cooling bath was removed and the resulting mixture was stirred at 25° C. for 4 hours and the solvent was evaporated. The resulting residue was suspended in hexanes (100 mL) and washed with warm water (42° C., 3×100 mL). The hexane layer was separated, dried over Na$_2$SO$_4$, filtered, and evaporated to provide the product (1.85 g). $^1$HNMR (400 MHz, CDCl$_3$): δ(ppm) 7.20-7.15 (m, 3H), 7.05-6.94 (m, 7H), 6.84-6.80 (m, 2H), 6.09 (br-s,1H), 4.49 (d, 1H), 3.99-3.91 (m, 3H), 2.87-2.79 (m, 1H), 1.21 (d, 6H), 1.17 (d, 6H), 1.08 (d, 6H). LC/MS: 479 (m/z).

B. Preparation of Triethylamine and Formic Acid Mixture.

Formic acid (15 mL) was cooled to 10° C. (internal) under nitrogen. Triethylamine (21.9 mL) was added to the formic acid at a rate so as to maintain the temperature below 25° C. (~40 minutes). The resulting mixture was stirred overnight at room temperature. The mixture was degassed by applying vacuum for 1 hour, sparging with N$_2$ for 30 minutes, and then again applying vacuum for 1 hour and sparging with N$_2$ for 30 minutes.

C. Preparation of Degassed Dimethylformamide.

Dimethylformamide (20 mL) was degassed by applying vacuum for 1 hour, sparging with N$_2$ for 30 min, and then again applying vacuum for 1 hour and sparging with N$_2$ for 30 minutes.

D. Catalyst Preparation.

Dichloro(p-cymene)ruthenium(II) dimer (44 mg) and N-((1R,2R)-2-amino-1,2-diphenyl-ethyl)-2,4,6-triisopropyl-benzenesulfonamide (92 mg) were taken in 20 mL screw cap vial with septum and flushed with N$_2$. Dimethylformamide (2 mL, degassed) was added, the mixture stirred at 80° C. for 30 minutes and cooled to room temperature.

E. Chiral Reduction.

[4-(3,4-Dichloro-benzyloxy)-phenyl]-oxo-acetic acid methyl ester (10 g) was degassed by applying vacuum for 20 minutes and purging with N$_2$ for 20 minutes. A triethylamine-formic acid mixture (15 mL, degassed) and dimethylformamide (13 mL, degassed) were added to the ketone at 25° C. under a continuous nitrogen flow and stirred for 15 minutes. The mixture was cooled to 4° C. (internal), the catalyst mixture (above) was added (no temperature fluctuation observed), and the mixture stirred at 5° C. for 16 hours with a continuous nitrogen flow. Water (60 mL) was added slowly, the mixture stirred for 5 minutes and the product was extracted with ethyl acetate (100 mL). The ethyl acetate layer was washed with water (100 mL) and brine (60 mL), dried over Na$_2$SO$_4$, filtered and evaporated. The residue (thick brown syrup) was dissolved in MTBE (10 mL) and hexanes was added (100 mL) with constant stirring. The compound initially precipitated as an oil, but stirring for 2-3 hours provided a well dispersed solid. The solid was filtered and washed with hexanes (2×20 mL). The solid was dried on rotavap at 40° C. for 1 hour (8.7 g, ee 96.6%). $^1$H NMR (400 MHz, CDCl$_3$): δ(ppm) 7.54 (d, 1H), 7.46 (d, 1H), 7.35 (d, 2H), 7.28-7.24 (m, 1H), 6.95 (d, 2H), 5.14 (d, 1H), 5.02 (s, 2H), 3.77 (s, 3H), 3.37 (d, 1H). The ee was determined by chiral HPLC: chiralpak OD-H, 25 cm×4.6 mm column with 90:10 hexane/IPA mobile phase (isocratic), 1.0 mL/minute flow rate, 45.0 minute run time, column T=40° C., wavelengths of detection: 254 nm and 230 nm (note: all the wavelengths subtract a reference at 360 nm).

The invention claimed is:
1. A compound of Formula (I)

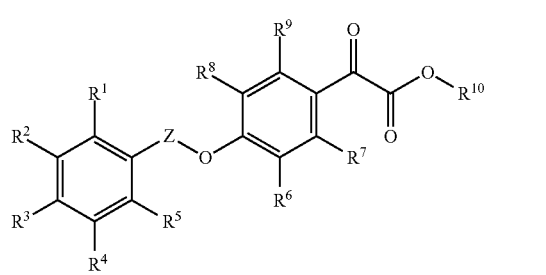

wherein:
R$^1$ is hydrogen, fluoro, chloro, methyl, ethyl, isopropyl, methoxy, ethoxy, isopropoxy, trifluoromethyl, or trifluoromethoxy;

$R^5$ —is hydrogen, fluoro, chloro, methyl, ethyl, isopropyl, methoxy, ethoxy, isopropoxy, trifluoromethyl, or trifluoromethoxy;

$R^3$ is hydroxyl, cyano, fluoro chloro, methyl, ethyl, isopropyl, methoxy, ethoxy, isopropoxy, trifluoromethyl, or trifluoromethoxy;

one of $R^2$ and $R^4$ is hydrogen, hydroxyl, cyano, fluoro, chloro, methyl, ethyl, isopropyl, methoxy, ethoxy, isopropoxy, trifluoromethyl, or trifluoromethoxy, while the other is hydrogen hydroxyl, cyano, fluoro, chloro, methyl, ethyl, isopropyl, methoxy, ethoxy, isopropoxy, trifluoromethyl, or trifluoromethoxy;

$R^6$, $R^7$, $R^8$, $R^9$ are hydrogen;

$R^{10}$ is hydrogen, $C_{1-6}$ alkyl, or an alkali metal cation; and

Z is— unsubstituted methylene or unsubstituted 1,2-ethylene.

2. The compound of claim 1, where $R^1$ and $R^5$ are independently selected from the group consisting of hydrogen and chloro.

3. The compound of claim 2, where $R^2$ is hydrogen and $R^4$ is chloro, or $R^2$ is chloro and $R^4$ is hydrogen.

4. The compound of claim 3, where $R^3$ is chloro.

5. The compound of claim 4, where $R^{10}$ is methyl.

6. The compound of claim 1, where Z is methylene.

\* \* \* \* \*

UNITED STATES PATENT AND TRADEMARK OFFICE
CERTIFICATE OF CORRECTION

PATENT NO. : 9,162,963 B2
APPLICATION NO. : 13/934491
DATED : October 20, 2015
INVENTOR(S) : Polisetti et al.

It is certified that error appears in the above-identified patent and that said Letters Patent is hereby corrected as shown below:

Claims

In column 11, line 1, in claim 1, delete "R5—is" and insert -- R5 is --, therefor.

In column 11, line 4, in claim 1, delete "fluoro chloro" and insert -- fluoro, chloro --, therefor.

In column 11, line 10, in claim 1, delete "hydrogen hydroxyl" and insert -- hydrogen, hydroxyl --, therefor.

In column 11, line 15, in claim 1, delete "is—" and insert -- is --, therefor.

In column 11, lines 15-16, in claim 1, delete "1,2 -ethylene." and insert -- 1,2-ethylene. --, therefor.

In column 11, line 17, in claim 2, delete "Rl" and insert -- R1 --, therefor.

Signed and Sealed this
Fifth Day of April, 2016

Michelle K. Lee
*Director of the United States Patent and Trademark Office*